United States Patent [19]

Neuzil

[11] 4,386,225

[45] May 31, 1983

[54] PROCESS FOR THE SEPARATION OF CRESOL FROM XYLENOL

[75] Inventor: Richard W. Neuzil, Downers Grove, Ill.

[73] Assignee: UOP Inc., Des Plaines, Ill.

[21] Appl. No.: 338,796

[22] Filed: Jan. 11, 1982

[51] Int. Cl.$^3$ .............................................. C07C 37/82
[52] U.S. Cl. ..................................... 568/758; 568/750; 568/751
[58] Field of Search ......................... 568/758, 750, 751

[56] References Cited

U.S. PATENT DOCUMENTS

| | | | |
|---|---|---|---|
| 2,985,589 | 5/1961 | Broughton et al. | 210/34 |
| 3,014,078 | 12/1961 | Fleck et al. | 260/621 |
| 3,201,491 | 8/1965 | Stine et al. | 260/676 |
| 3,265,750 | 8/1966 | Peck et al. | 260/666 |
| 3,510,423 | 4/1968 | Neuzil et al. | 208/310 |
| 3,558,730 | 1/1971 | Neuzil | 260/674 |
| 3,558,732 | 1/1971 | Neuzil | 260/674 |
| 3,626,020 | 12/1971 | Neuzil | 260/674 SA |
| 3,668,267 | 6/1972 | Hedge | 260/674 SA |
| 3,686,342 | 8/1972 | Neuzil | 260/674 SA |
| 3,969,422 | 7/1976 | Neuzil et al. | 260/621 B |
| 4,124,770 | 11/1978 | Miyake et al. | 568/758 |

FOREIGN PATENT DOCUMENTS

| | | | |
|---|---|---|---|
| 55-151522 | 11/1980 | Japan | 568/758 |
| 56-45430 | 4/1981 | Japan | 568/758 |
| 56-45432 | 4/1981 | Japan | 568/758 |
| 2058772 | 4/1981 | United Kingdom | 568/750 |

*Primary Examiner*—Werren B. Lone
*Attorney, Agent, or Firm*—James R. Hoatson, Jr.; Louis A. Morris; William H. Page, II

[57] ABSTRACT

A process for the separation of at least one cresol isomer from a feed mixture containing the cresol and xylenol which process employs a crystalline aluminosilicate adsorbent to selectively adsorb the cresol from the feed mixture. The process employs a desorbent material to recover the cresol. The process may employ a simulated moving bed flow scheme.

5 Claims, No Drawings

PROCESS FOR THE SEPARATION OF CRESOL FROM XYLENOL

BACKGROUND OF THE INVENTION

1. Field of the Invention

The field of art to which the claims invention pertains is solid-bed adsorptive separation with an adsorbent comprising a zeolite. More specifically, the claimed invention relates to an improved process for the separation of a cresol from xylenol by employing a solid crystalline aluminosilicate adsorbent which selectively removes the cresol from the feed mixture. The cresol may then be recovered from the adsorbent through a desorption step which employs a desorbent material.

2. Description of the Prior Art

It is known in the separation art that certain crystalline aluminosilicates can be used to separate hydrocarbon species from mixtures thereof. In particular, the separation of normal paraffins from branched chain paraffins can be accomplished by using the type A zeolites which have pore openings from 3 to about 5 Angstroms. Such a separation process is disclosed for example in U.S. Pat. Nos. 2,985,589 and 3,201,491. These adsorbents allow a separation based on the physical size differences in the molecules by allowing the smaller or normal hydrocarbons to be passed into the cavities within the crystalline aluminosilicate adsorbent, while excluding the larger or branched chain molecules.

U.S. Pat. Nos. 3,265,750 and 3,510,423 for example disclose processes in which larger pore diameter zeolites such as the type X or type Y structured zeolites can be used to separate olefinic hydrocarbons.

The type X or type Y zeolites have additionally been employed in processes to separate individual hydrocarbon isomers. In the processes described in U.S. Pat. Nos. 3,558,730; 3,558,732; 3,626,020; and 3,686,342, for example, they are used to separate desired xylene isomers; in U.S. Pat. No. 3,668,267 they are used to separate particular alkyl substituted naphthalenes.

More specifically, U.S. Pat. Nos. 3,014,078 and 3,969,422 teach the separation of cresol isomers by employing an adsorbent consisting of a crystalline zeolitic metalloaluminosilicate to selectively adsorb a cresol isomer from a feed mixture thereby producing a rich (cresol associated) adsorbent. In the preferred mode of operation, the adsorbed isomer is then removed by contacting with a displacement exchange fluid. Preferred displacement exchange fluids include phenol and alcohol, although other materials which may be employed include ethers, aromatic hydrocarbons, and paraffin hydrocarbons.

The present invention relates to a process for separating a cresol from a xylenol. In particular it has been found that a crystalline aluminosilicate is selective for cresol isomers as compared to xylenol isomers and may therefore be employed for separating cresols from xylenols.

SUMMARY OF THE INVENTION

In brief summary, the present invention is, in one embodiment, a process for separating a cresol from a feed mixture containing the cresol and a xylenol which process comprises contacting the feed, at adsorption conditions, with an adsorbent comprising a crystalline aluminosilicate, thereby selectively adsorbing the cresol and thereafter removing the xylenol from contact with the adsorbent.

In the second embodiment the present invention is a process for separating a cresol from a mixture containing the cresol and a xylenol which process employs an adsorbent comprising a crystalline aluminosilicate which process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed input stream at an upstream boundary of the zone and a raffinate output stream at a downstream boundary of the zone; (c) maintaining a purification zone immediately upstream from the adsorption zone, the purification zone defined by the adsorbent located between an extract output stream at an upstream boundary of the purification zone and the feed input stream at a downstream boundary of the purification zone; (d) maintaining a desorption zone immediately upstream from the purification zone, the desorption zone defined by the adsorbent located between a desorbent input stream at an upstream boundary of the zone and the extract output stream at a downstream boundary of the zone; (e) passing the feed mixture into the adsorption zone at adsorption conditions and effecting the selective adsorption of the cresol by the adsorbent in the adsorption zone and withdrawing a raffinate output stream from the adsorption zone; (f) passing a desorbent material into the desorption zone at desorption conditions to effect the displacement of the cresol from the adsorbent in the desorption zone; (g) withdrawing an extract output stream comprising the cresol and desorbent material from the desorption zone; (h) periodically advancing through the column of adsorbent in a downstream direction with respect to fluid flow in the adsorption zone, the feed input stream, raffinate output stream, desorbent input stream, and extract output stream to effect the shifting of zones through the adsorbent and the production of extract output and raffinate output streams.

Other embodiments and objects of the present invention encompass details about feed mixtures, adsorbents, desorbent materials, and operating conditions all of which are hereinafter disclosed in the following discussion of each of these facets of the present invention.

DESCRIPTION OF THE INVENTION

Adsorbents which can be used in the adsorptive separation of cresols from xylenols (including ethylphenol) which is herein considered as a xylenol) in accordance with the present invention are certain crystalline aluminosilicates or molecular sieves including both the natural and synthetic aluminosilicates. Such crystalline aluminosilicates have cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as molecular sieves and separations performed with molecular sieves are generally thought to take place by a physical "sieving" of smaller from larger molecules appearing in the feed mixture. Separation may also occur because of differences in electrochemical attraction of the different feed mixture ingredients and the adsorbent rather than on pure physical size differences in the ingredient molecules.

In hydrated form, the preferred crystalline aluminosilicates generally encompass those zeolites represented by the Formula 1 below:

Formula 1

$$M_{2/n}O:Al_2O_3:wSiO_2:yH_2O$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The cations may be any one of a number of cations which will hereinafter be described in detail.

Adsorbents comprising the type X structured and type Y structured zeolites are especially preferred for the adsorptive separation of the present invention. These zeolites are described and defined in U.S. Pat. Nos. 2,882,244 and 3,120,007 respectively. The terms "type X structured" and "type Y structured" zeolites as used herein shall include all zeolites which have a general structure as represented in the above two cited patents and additionally shall specifically include crystalline aluminosilicates produced from either of the zeolites described in the two patents as starting materials by various ion-exchange techniques or thermal treatments or combinations thereof.

The type X structured zeolites can be represented in terms of mole oxides as represented in Formula 2 below:

Formula 2

$$(0.9\pm0.2)M_{2/n}O:Al_2O_3:(2.5\pm0.5)SiO_2:yH_2O$$

where "M" represents at least one cation having a valence of not more than 3, "n" represents the valence of "M" and "y" is a value up to about 9 depending upon the identity of "M" and the degree of hydration of the crystalline structure.

The type Y structured zeolites can be represented in terms of the mole oxides for the sodium form as represented by Formula 3 below:

Formula 3

$$(0.9\pm0.2)Na_2O:Al_2O_3:wSiO_2:yH_2O$$

where "w" is a value of greater than about 3 up to 8, and "y" may be any value up to about 9.

Adsorbents contemplated herein include not only the sodium form of the type X and the type Y zeolites but also crystalline materials obtained from such zeolites by partial or complete replacement of the sodium at the exchangeable cationic sites with one or more other specified cations. The term "exchangeable cationic sites" generally refers to the sites occupied by sodium cations present in the type X and type Y zeolites as indicated in Formula 2 and Formula 3 above. Most of the sodium cations originally present at these sites can be replaced or exchanged with other cations.

Cationic or base exchange methods are generally known to those familiar with the field of crystalline aluminosilicate production. They are generally performed by contacting the zeolite with an aqueous solution of the soluble salts of the cation or cations desired to be placed upon the zeolite. The desired degree of exchange takes place and then the sieves are removed from the aqueous solution, washed and dried to a desired water content. It is contemplated that cation exchange operations may take place using individual solutions of desired cations to be placed on the zeolite or using an exchange solution containing a mixture of cations, where two or more desired cations are to be placed on the zeolite.

The cations which may be placed upon the zeolite for use in the process of the present invention include cations in the group sodium, potassium, magnesium, calcium, strontium, and barium. In the process of this invention it has been found that an adsorbent comprising a type X zeolite containing barium and potassium at the exchangeable cationic sites is particularly preferred.

When singular cations are base exchanged upon a zeolite the singular cations can comprise anywhere from 5 up to 75 wt.% on a relative volatile free basis of the zeolite depending upon the molecular weight of the material exchanged upon the zeolite. It is contemplated that when single ions are placed upon the zeolite that they may be on the zeolite in concentrations of from about 1% to about 100% of the original cations present (generally sodium) upon the zeolite prior to its being ion-exchanged. By knowing the empirical formula of the zeolite used, its water content and the percentage of any amorphous material or binder present, if any, it is possible to calculate the percentage of ion exchange that has taken place.

When two or more cations are placed upon the zeolite there are two parameters in which one can operate in order to effectively produce a zeolite having the maximum selective properties. One of the parameters is the extent of the zeolite ion exchange which is determined by variables such as the length of ion-exchange times, ion-exchange temperature, and cation concentration. The other parameter is the ratio of individual cations placed on the zeolite. In the preferred embodiment of the present invention where the cation pair comprises barium and potassium the weight ratio of barium to potassium upon the zeolite can vary anywhere from about less than one up to about one hundred.

The separation process of the present invention is particularly useful for removing cresol contaminant from 2,6-xylenol obtained from a coal gasification process. The cresol includes ortho-, meta-, and paraisomers and may comprise up to about 10 vol.% of the cresol-xylenol feed mixture to the process of the present invention. Xylenol is useful for the preparation of coal tar disinfectants and the manufacture of artificial resins.

To separate cresol from a feed mixture containing cresol and xylenol in accordance with the present invention the mixture is contacted with an adsorbent comprising a crystalline aluminosilicate and the cresol is more selectively adsorbed and retained by the adsorbent while the xylenol is relative unadsorbed and is removed from the interstitial void spaces between the particles of adsorbent and the surface of the adsorbent. The adsorbent containing the more selectively adsorbed cresol is referred to as a "rich" adsorbent—rich in the more selectively adsorbed cresol. It is essentially impossible to achieve this separation by conventional distillation methods because of the closeness of the relative volatilities of cresol and xylenol.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as raffinate components all of the feed mixture xylenols and the extract stream will contain cresols as the extract component.

Although it is possible by the process of this invention to produce high purity (98% or greater) xylenols at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed cresol to the concentration of less selectively adsorbed xylenols will be highest in the extract stream, next highest in the feed mixture, and lowest in the raffinate stream. Likewise, the ratio of the less selectively adsorbed xylenols to the more selectively adsorbed cresol will be highest in the raffinate stream, next highest in the feed mixture, and the lowest in the extract stream.

The adsorbent can be contained in one or more chambers where through programmed flow into and out of the chambers separation of cresol is effected. The adsorbent will preferably be contacted with a desorbent material which is capable of displacing the adsorbed cresol from the adsorbent. An extract stream comprising cresol and desorbent material will then be withdrawn from the adsorbent and the desorbent material separated and recovered. Alternatively, the cresol could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and a desorbent material (hereinafter described in more detail). In the simplest embodiment of the invention the adsorbent is employed in the form of a single static bed in which case the process is only semicontinuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference thereto. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream across lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of our process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a donwstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well known to the separation art.

Reference can be made to the aforementioned D. B. Broughton U.S. Pat. No. 2,985,589, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 40° C. to about 260° C. and a pressure range sufficient to maintain liquid phase, preferably from about atmospheric to about 500 psig. Desorption conditions will include the same range of temperatures and pressures as used for adsorption conditions.

The size of the units which can utilize the process of this invention can vary anywhere from those of pilot-plant scale (see for example our assignee's U.S. Pat. No. 3,706,812) to those of commercial scale and can range in flow rates from as little as a few cc an hour up to many thousands of gallons per hour.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressure or both to effectively purge the adsorbed feed component from the adsorbent.

However, in process which are generally operated at substantially constant pressures and temperatures to insure liquid phase, the desorbent material relied upon must be judiciously selected in order that it may displace the adsorbed feed component from the adsorbent with reasonable mass flow rates without itself being so strongly adsorbed as to unduly prevent the extract component from displacing the desorbent material in a following adsorption cycle.

Desorbent materials which can be used in the process of this invention should additionally be substances which are easily separable from the feed mixture that is passed into the process. In desorbing the preferentially adsorbed component of the feed, both desorbent material and the extract component are removed in admixture from the adsorbent. Without a method of separation such as distillation of these two materials, the purity of the desorbent material recovered for reuse would not be very high since it would be contaminated with extract component. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture, although for the process of this invention it is preferred that desired desorbent material have a boiling range less than that of the feed material. A particularly effective desorbent material for use in the process of the present invention is 1-pentanol.

Capacity of the adsorbent for adsorbing a specific volume of an extract component is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity for one component as compared to another component. Some adsorbents demonstrate acceptable capacity but possess little or no selectivity. Relative selectivity can be expressed not only for one feed mixture component as compared to another but can also be expressed between any feed mixture component and the desorbent. The relative selectivity, (B), as used throughout this specification is defined as the ratio of two components of an adsorbed phase over the ratio of the same two components in an unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } C]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Desorbent materials ideally would have a selectivity equal to about 1 or slightly less than 1 with respect to an extract component.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

It is also necessary that the adsorbent possess little or no catalytic activity toward any reaction such as polymerization or isomerization of any of the feed components. Such activity might effect adsorbent capacity or selectivity or product yields or all of these, but in the adsorptive separation of cresol from xylenol with a zeolite-containing adsorbent this is generally not a problem.

To best evaluate promising adsorbent systems and to translate this type of data into a practical cresol-xylenol separation process, actual testing of the best systems in a continuous countercurrent liquid-solid contacting device is required. The general operating principles of such a device have been previously described and are found in Broughton U.S. Pat. No. 2,985,589. A specific laboratory-size fluid-solid contacting apparatus utilizing these principles is described in deRosset et al U.S. Pat. No. 3,706,812. The apparatus comprises multiple adsorbent beds with a number of access lines attached to distributors within the beds and terminating at a rotary distributing valve. At a given value position, feed and desorbent are being introduced through two of the lines and raffinate and extract are withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on adsorbent testing and evaluation techniques may be found in the paper "Separation of $C_8$ Aromatics by Adsorption" by A. J. deRosset, R. W. Neuzil, A. J. Korous, and D. H. Rosback presented at the American Chemical Society, Los Angeles, Calif., Mar. 28–Apr. 2, 1971.

The improved process of this invention as applied to separating cresol from a feed mixture containing the cresol isomers and 2,6-xylenol was demonstrated by actual continuous testing in the apparatus described above as set forth in the following examples:

EXAMPLE I

Data for this example was obtained using the above described laboratory-size simulated moving bed apparatus. An Na-Y zeolite was used as the adsorbent and 1-pentanol the desorbent. The feed mixture was a crude xylenol composition comprising 92 vol.%, 2,6-xylenol, 0.4 vol.% o-cresol, 3.5 vol.% p-cresol and 4.1 vol.% m-cresol mixed with toluene to the extent that toluene was 40 vol.% of the feed mixture. The toluene served to prevent crystallization of the components of the feed solution. Following is the data obtained during the test run.

| Temperature °C. | 171 | 170 | 170 | 150 | 150 | 150 |
|---|---|---|---|---|---|---|
| $L_2/A$* | 1.11 | 1.31 | 1.67 | 1.37 | 1.39 | 1.54 |
| A/F** | 0.92 | 0.89 | 0.86 | 0.91 | 0.88 | 0.89 |
| Raffinate | | | | | | |
| % 2,6-xylenol | 99+ | 99.0 | 98.0 | 99.0 | 97.6 | 96.8 |
| Yield (%) | 98 | 99 | 99 | 99 | 99 | 99 |
| Extract (%) | | | | | | |
| 2,6-xylenol | 15.6 | 9.2 | 11.4 | 13.9 | 12.4 | 15.3 |
| o-cresol | 1.5 | 1.1 | — | 0.4 | — | — |
| p-cresol | 38.2 | 51.8 | 74.3 | 53.3 | 66.4 | 66.4 |
| m-cresol | 44.7 | 37.9 | 14.3 | 32.4 | 21.2 | 18.3 |

*Zone 2 reflux rate
**ratio of the selective pore volume circulation rate to feed rate (based on total crude xylenol volume, not the total feed volume of 40% toluene +60% crude xylenol)

EXAMPLE II

A second test run identical in all respects to the first was run except that the adsorbent used was a K-Ba-X zeolite. Following is the data that was obtained:

| Temperature °C. | 150 | 150 | 150 | 150 | 150 |
|---|---|---|---|---|---|
| $L_2/A$ | 1.14 | 0.84 | 0.63 | 0.84 | 1.01 |
| A/F | 0.91 | 0.98 | 0.47 | 0.45 | 0.46 |
| Raffinate | | | | | |
| % 2,6-xylenol | 99.3 | 99.8 | 99.9 | 99.8 | 97.3 |
| Yield (%) | 99.8 | 99.7 | 95.6 | 99.8 | 99.8 |
| Extract (%) | | | | | |
| 2,6-xylenol | 2.9 | 3.2 | 33.8 | 2.1 | 2.6 |
| o-cresol | — | 6.2 | 3.9 | 5.7 | 0.9 |
| p-cresol | 89.3 ⎫ | ⎫ 90.6 | 27.9 ⎫ | ⎫ 92.2 | 96.5 |
| m-cresol | 7.8 ⎭ | ⎭ | 34.4 ⎭ | ⎭ | |

Examination of the data from the test runs indicate that of the two adsorbents evaluated, the K-Ba-X zeolite displayed better overall performance charcteristics than the corresponding Na-Y. This is evident when the purity-yield relationship of the two runs at the 150° C. process temperature is compared. For the K-Ba-X adsorbent 2,6-xylenol purities of 99.5+% at yields of 99.5+% were consistently obtained whereas for the Na-Y, purities of only 99.0% at yields of 99% were the best obtainable. This fact is made more apparent if the 2,6-xylenol present in the extracts is examined. For the K-Ba-X adsorbent the percentage of 2,6-xylenol in the extract was around 2 to 3% whereas for the Na-Y it was between 10 to 15%. Also, the feed rate for the K-Ba-X adsorbent was nearly twice as great, A/F of 0.45 vs. 0.90 for the Na-Y.

The reasons for the better performance of the K-Ba-X adsorbent over that of the Na-Y is considered due to the faster rates of desorption for the former. This is indicated by the substantially higher $L_2/A$ required for the Na-Y as compared to that required for the K-Ba-X.

Although not apparent from the data presented above, the concentration profiles present in the Na-Y column indicated a great deal of "tailing" of the extract and raffinate components in both Zones II to III as compared to those for the column packed with K-Ba-X adsorbent.

The invention claimed is:

1. A process for separating a cresol from a mixture containing up to 10 wt.% of said cresol and a xylenol which process employs an adsorbent comprising a Type X zeolite having barium and potassium cations at the exchangeable ionic sites, which process comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture into said adsorption zone at a temperature in the range of from about 40° to about 260° C. and a pressure in the range of from about atmospheric pressure to about 500 psig and effecting the selective adsorption of said cresol by said adsorbent in said adsorption zone and withdrawing a raffinate output stream from said adsorption zone;

(f) passing a desorbent material having a substantially different average boiling point than the cresol and xylenol components of the feed stream into said desorption zone at a temperature within the range of from about 40° to about 260° C. and a pressure in the range of from about atmospheric pressure to about 500 psig to effect the displacement of said cresol from the adsorbent in said desorption zone;

(g) withdrawing an extract output stream comprising said cresol and desorbent material from said desorption zone;

(h) periodically advancing through said column of adsorbent in a downstream direction with respect to fluid flow in said adsorption zone, the feed input stream, raffinate output stream, desorbent input stream, and extract output stream to effect the shifting of zones through said adsorbent and the production of extract output and raffinate output streams.

2. The process of claim 1 wherein said feed mixture contains ortho-, meta-, and para-cresol.

3. The process of claim 1 wherein said xylenol comprises 2,6-xylenol.

4. The process of claim 1 wherein said desorbent fluid comprises 1-pentanol.

5. The process of claim 1 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

* * * * *